US009579170B2

(12) United States Patent
Van Lierde et al.

(10) Patent No.: US 9,579,170 B2
(45) Date of Patent: Feb. 28, 2017

(54) METHOD FOR CREATING A PERSONALIZED DIGITAL PLANNING FILE FOR SIMULATION OF DENTAL IMPLANT PLACEMENT

(75) Inventors: Carl Van Lierde, Meerbeke (BE); Bert Van Roie, Leuven (BE)

(73) Assignee: Materialise Dental N.V., Leuven (BE)

( * ) Notice: Subject to any disclaimer, the term of this patent is extended or adjusted under 35 U.S.C. 154(b) by 653 days.

(21) Appl. No.: 12/301,293

(22) PCT Filed: Apr. 30, 2007

(86) PCT No.: PCT/EP2007/003810
§ 371 (c)(1),
(2), (4) Date: Nov. 18, 2008

(87) PCT Pub. No.: WO2007/134701
PCT Pub. Date: Nov. 29, 2007

(65) Prior Publication Data
US 2009/0187393 A1 Jul. 23, 2009

(30) Foreign Application Priority Data

May 19, 2006 (GB) .................... 0609988.1

(51) Int. Cl.
*A61C 13/00* (2006.01)
*A61C 1/08* (2006.01)
(Continued)

(52) U.S. Cl.
CPC .......... *A61C 13/0004* (2013.01); *A61C 1/084* (2013.01); *A61C 9/0053* (2013.01); *A61C 19/04* (2013.01)

(58) Field of Classification Search
CPC ..... A61C 1/084; A61C 13/0004; A61C 19/04; A61C 9/004
(Continued)

(56) References Cited

U.S. PATENT DOCUMENTS

| 4,109,382 A | 8/1978 | Koch |
| 4,872,840 A | 10/1989 | Bori |

(Continued)

FOREIGN PATENT DOCUMENTS

| BE | 09400399 | 4/1994 |
| BE | 1011205 | 6/1999 |

(Continued)

OTHER PUBLICATIONS

Goebel et al., Background Removal in Dental Panoramic X-ray Images by the A-Trous Multiresolution Transform, Circuit Theory and Design, 2005. Proceedings of the 2005 European Conference, Aug. 28-Sep. 2, 2005.*

(Continued)

*Primary Examiner* — Bo J Peng
(74) *Attorney, Agent, or Firm* — Clark & Elbing LLP

(57) ABSTRACT

The present invention provides a method for creating a personalized digital planning file for simulation of dental implant placement. After planning, the digital representation in a plaster model may be used to design and produce dedicated surgical templates to assist the surgeon in transferring the implant plan to a patient during medical intervention.

11 Claims, 7 Drawing Sheets

(51) Int. Cl.
*A61C 9/00* (2006.01)
*A61C 19/04* (2006.01)

(58) Field of Classification Search
USPC .......................................................... 703/11
See application file for complete search history.

(56) References Cited

U.S. PATENT DOCUMENTS

| | | |
|---|---|---|
| 4,955,811 A | 9/1990 | Lazzara et al. |
| 4,988,297 A | 1/1991 | Lazzara et al. |
| 5,102,271 A | 4/1992 | Hemmings |
| 5,133,660 A | 7/1992 | Fenick |
| 5,184,926 A | 2/1993 | Hemmings |
| 5,213,502 A | 5/1993 | Daftary |
| 5,215,460 A | 6/1993 | Perry |
| 5,259,759 A | 11/1993 | Jörneus et al. |
| 5,320,529 A | 6/1994 | Pompa |
| 5,520,688 A | 5/1996 | Lin |
| 5,554,027 A | 9/1996 | Brånemark |
| 5,562,448 A | 10/1996 | Mushabac |
| 5,564,925 A | 10/1996 | Shampanier et al. |
| 5,584,694 A | 12/1996 | Forsmalm et al. |
| 5,613,852 A | 3/1997 | Bavitz |
| 5,662,473 A | 9/1997 | Rassoli |
| 5,674,071 A | 10/1997 | Beaty et al. |
| 5,685,714 A | 11/1997 | Beaty et al. |
| 5,725,376 A | 3/1998 | Poirier |
| 5,733,122 A | 3/1998 | Gordon |
| 5,769,636 A | 6/1998 | Di Sario |
| 5,800,168 A | 9/1998 | Cascione et al. |
| 5,813,858 A | 9/1998 | Singer |
| 5,823,778 A | 10/1998 | Schmitt et al. |
| 5,871,356 A | 2/1999 | Guedj |
| 5,967,777 A | 10/1999 | Klein et al. |
| 5,989,025 A | 11/1999 | Conley |
| 5,989,258 A | 11/1999 | Hattori |
| 6,062,856 A | 5/2000 | Sussman |
| 6,319,000 B1 | 11/2001 | Brånemark |
| 6,319,006 B1 | 11/2001 | Scherer et al. |
| 6,322,359 B1 * | 11/2001 | Jordan et al. ................... 433/73 |
| 6,361,537 B1 | 3/2002 | Anderson |
| 6,382,975 B1 | 5/2002 | Poirier |
| 6,447,295 B1 | 9/2002 | Kumar et al. |
| 6,514,258 B1 | 2/2003 | Brown et al. |
| 6,692,254 B1 | 2/2004 | Kligerman et al. |
| 6,814,575 B2 | 11/2004 | Poirier |
| 7,063,532 B1 * | 6/2006 | Jones et al. ...................... 433/24 |
| 2002/0102517 A1 | 8/2002 | Poirier |
| 2002/0114425 A1 * | 8/2002 | Lang et al. ...................... 378/56 |
| 2002/0137003 A1 | 9/2002 | Knapp |
| 2004/0146830 A1 | 7/2004 | Weinstein |
| 2004/0197727 A1 * | 10/2004 | Sachdeva et al. ............... 433/24 |
| 2005/0106534 A1 | 5/2005 | Gahlert |
| 2005/0170311 A1 | 8/2005 | Tardieu et al. |
| 2006/0040233 A1 | 2/2006 | Weinstein et al. |
| 2006/0093988 A1 | 5/2006 | Swaelens et al. |
| 2006/0275736 A1 | 12/2006 | Wen et al. |
| 2007/0160953 A1 | 7/2007 | Tardieu |
| 2009/0187393 A1 | 7/2009 | Van Lierde et al. |

FOREIGN PATENT DOCUMENTS

| | | |
|---|---|---|
| DE | 100 36 027 A1 | 1/2002 |
| EP | 640 322 | 3/1995 |
| JP | 2000-512868 | 10/2000 |
| JP | 2005-168518 | 6/2005 |
| WO | WO 92/03984 | 3/1992 |
| WO | WO 97/10770 | 3/1997 |
| WO | WO 97/49351 | 12/1997 |
| WO | WO 99/26540 | 6/1999 |
| WO | WO 00/25695 | 5/2000 |
| WO | WO 03/071972 | 9/2003 |
| WO | WO 2004/064660 | 8/2004 |
| WO | WO 2004/065893 | 8/2004 |
| WO | WO 2004/075771 | 9/2004 |
| WO | WO 2005/053564 | 6/2005 |
| WO | WO 2006/115841 | 11/2006 |
| WO | WO 2007/134701 | 11/2007 |

OTHER PUBLICATIONS

Whitepaper, 2D and 3D Texture Mapping Support, http://www.okino.com/new/toolkit/1-11.htm, Feb. 16, 2004.*
Advisory Action for U.S. Appl. No. 10/505,846, issued Sep. 17, 2010.
Notice of Grounds of Rejection for Japanese Patent Application No. 2006-501389, dated Jan. 26, 2010.
English Translation of the Notice of Grounds of Rejection for Japanese Patent Application No. 2006-501389, dated Jan. 26, 2010.
Office Action for Canadian Patent Application No. 2,477,107, dated Dec. 15, 2010.
Office Action for U.S. Appl. No. 10/546,702, issued Jan. 20, 2011.
Office Action for U.S. Appl. No. 12/421,919, issued Apr. 29, 2011.
Notice of Preliminary Rejection for Korean Patent Application No. 10-2004-7013405 issued by the KIPO, dated Oct. 28, 2009.
English translation of the Notice of Preliminary Rejection for Korean Patent Application No. 10-2004-7013405 issued by the KIPO, dated Oct. 28, 2009.
Communication from European Patent Office regarding EP 04 713 496.0, dated Jan. 22, 2009.
International Preliminary Report on Patentability (PCT/FR2003/000667), completed Oct. 17, 2003.
International Preliminary Report on Patentability (PCT/BE2004/000024), completed Sep. 19, 2005.
International Preliminary Report on Patentability (PCT/EP2004/013435), mailed Mar. 16, 2006.
International Preliminary Report on Patentability (PCT/EP2007/003810), completed Nov. 14, 2008.
International Search Report (PCT/FR2003/000667), mailed Jul. 28, 2003.
International Search Report (PCT/BE2004/000024), mailed Jul. 23, 2004.
International Search Report (PCT/EP2004/013435), mailed Jul. 4, 2005.
International Search Report (PCT/EP2007/003810), mailed Oct. 9, 2007.
Klein et al., "Computer-Guided Surgery Utilizing a Computer-Milled Surgical Template," *Pract. Proced. Aesthet. Dent.* 13(2): 165-169 (2001).
Office Action for Canadian Patent Application No. 2,477,107, dated Oct. 5, 2009.
Office Action for U.S. Appl. No. 10/505,846, mailed Mar. 21, 2008.
Office Action for U.S. Appl. No. 10/505,846, mailed Nov. 6, 2008.
Office Action for U.S. Appl. No. 10/505,846, mailed Jun. 19, 2009.
Office Action for U.S. Appl. No. 10/546,702, mailed Apr. 8, 2008.
Office Action for U.S. Appl. No. 10/546,702, mailed Nov. 13, 2008.
Office Action for U.S. Appl. No. 10/546,702, mailed May 8, 2009.
Office Action for U.S. Appl. No. 10/546,702, mailed Oct. 27, 2009.
Office Action for U.S. Appl. No. 10/596,124, mailed Dec. 5, 2007.
Office Action for U.S. Appl. No. 10/596,124, mailed Dec. 18, 2008.
Office Action for U.S. Appl. No. 10/596,124, mailed Jun. 19, 2009.
Response to Written Opinion for PCT/EP2004/013435, filed Jul. 20, 2005.
Translation of International Preliminary Report on Patentability (PCT/FR2003/000667), completed Oct. 17, 2003.
Translation of Notice of Grounds of Rejection for Japanese Patent Application No. 501389/2006, drafted Feb. 19, 2009.
Written Opinion of the International Searching Authority (PCT/BE2004/000024), mailed Jul. 23, 2004.
Written Opinion of the International Searching Authority (PCT/EP2004/013435), mailed Jul. 4, 2005.
Written Opinion of the International Searching Authority (PCT/EP2007/003810), mailed Oct. 9, 2007.
Office Action for U.S. Appl. No. 10/505,846, mailed on May 4, 2010.

(56) References Cited

OTHER PUBLICATIONS

Office Action for U.S. Appl. No. 10/546,702, mailed on Jun. 1, 2010.
Office Action for U.S. Appl. No. 12/421,919, mailed on Aug. 18, 2010.

* cited by examiner

US 9,579,170 B2

METHOD FOR CREATING A PERSONALIZED DIGITAL PLANNING FILE FOR SIMULATION OF DENTAL IMPLANT PLACEMENT

CROSS-REFERENCE TO RELATED APPLICATIONS

This application is the U.S. National Stage of International Application No. PCT/EP2007/003810, filed Apr. 30, 2007, which, in turn, claims the benefit of British Patent Application No. GB 0609988.1, filed May 19, 2006.

TECHNICAL FIELD OF THE INVENTION

The present invention relates to simulation of dental implant placement and more particularly relates to a method for creating a personalized digital planning file for simulation of dental implant placement as well as software for carrying out any of these methods and to computer systems implementing these methods.

BACKGROUND OF THE INVENTION

Surgical planning for dental implant placement traditionally uses medical imaging modalities to verify the quantity and quality of a jawbone. Multi-planar reformatted CT (computed tomography) has become one of the most comprehensive and accurate aids for implant treatment planning. CT offers means to visualise the oral anatomy of a patient in a number of differently oriented slices of a volumetric scan and to graphically superimpose on the images representations of commercial implants of varying length, diameter and brand (for example, SimPlant™ provided by Materialise, Leuven, Belgium).

According to the current state of the art a patient is sent to a radiologist for a CT scan. The result of the scan is a stack of 2D slices forming a three-dimensional volumetric "data set" which can then be used as input for a dental planning program. Typically, such a program imports the data set provided by a radiology site without altering any information. Using image-processing techniques such as, for example, image segmentation, three-dimensional models of the bone may be derived from the data set. In the planning environment, the practitioner subsequently defines a curve that follows the arch of the jaw. Several cross-sections can be chosen perpendicular to both the panoramic curve and the axial slices. Typically, implant receptor sites may be chosen in these cross-sections. The practitioner can modify the positions and inclinations of each implant as needed in any of the views, including the 3D view. Fine tuning is performed by shifting and tilting of the implant representations or by changing their dimensions. Each individual implant position can be evaluated in terms of the volume of available bone and its quality. The latter is interpretable in CT images by means of the number of Hounsfield units attributed to each of the voxels, i.e. volumetric building blocks of the CT images.

Disadvantages of using CT for dental implant planning are the additional costs related to scanning and the fact that significant irradiation of the patient is required in order to obtain the volumetric data. Moreover CT or CT-like scanning equipment, such as e.g. cone-beam scanners, is costly and has yet to be widely used in the dental market. Scanning equipment is therefore not always readily available.

To overcome these disadvantages methods for simulating dental implant placement without resorting to volumetric image data such as CT, cone-beam scans, MRI scans, have been proposed.

U.S. Pat. No. 6,319,006 describes a method for producing a drill assistance device for a tooth implant in which an X-ray image is correlated with a three-dimensional image of optically measured visible parts of a patient's remaining dentition. The method comprises taking an X-ray picture of the jaw and the compilation of corresponding measured data record, a three-dimensional, optical measurement of the visible surfaces of the jaw and of the teeth and the compilation of a corresponding measured data record. The measured data records from the X-ray picture and the measured data records from the three-dimensional, optical image are correlated with each other. Based on the information that is available, the type and position of the implant relative to the adjacent teeth is planned and a drill template is produced which is attached to the neighbouring teeth, thus making the exact drilling of an implant pilot hole possible.

However, a disadvantage of this way of working is the lack of three-dimensional information about the shape of the jawbone. While the X-ray image provides information about the bone in a projected image, it does not provide insights about the level of the bone in cross section along the dental arch. As an example, FIG. 1 shows two exemplary cross-sections of a jawbone, which on a frontal X-ray image would both be visualized identically. However the bone in both sections is very different as can be seen from FIG. 1.

In WO 2004/064660 a method for dental registration is provided. The method comprises rigidly coupling a base element to a maxillofacial area, inserting an object comprising at least one of a tool and a tool guide into a mouth in the maxillofacial area, and determining a position of the object relative to the rigid element without a reference element outside the mouth. According to embodiments, the method may comprise combining two non-volumetric images of at least part of the maxillofacial area. The non-volumetric images can be obtained by X-ray, optical scan data or direct bone surface measurements. The method may comprise acquiring the first non-volumetric image including at least a part of the base element, identifying at least one registration mark of the rigid element and registering the image to the second non-volumetric image, thereby registering the registration mark to the area.

The method described in WO 2004/064660 is tedious and not so practically convenient because a foreign object, i.e. the base element, needs to be introduced into the mouth and rigidly coupled to the jaw. The object furthermore needs to be present in the mouth during the imaging. Moreover, the technique does not take into account the fact that X-ray images inherently are inaccurate in the lateral direction, as disclosed in the book "Implants and Restorative Dentistry", Chapter 11—Imaging in oral implantology, page 178. A registration according to the described technique would not compensate for these inaccuracies.

SUMMARY OF THE INVENTION

It is an object of the present invention to provide a good method and apparatus for creating a personalized digital planning file for simulation of dental implant placement.

The above objective is accomplished by a method according to the present invention.

In a first aspect of the invention, a method is provided for creating a personalized digital planning environment for simulation of dental implant placement from (i) a digitised representation of an intra-oral surface anatomy of a patient including at least a part of the dental arch, (ii) an at least point-wise digital representation of soft tissue thickness in the region of and around potential dental implant receptor sites, and (iii) a two-dimensional dental X-ray image of the potential dental implant receptor sites, the method comprising:

mapping the two-dimensional dental X-ray image of the potential dental implant receptor sites along at least part of a dental arch of the digitized intra-oral surface anatomy, constructing a three-dimensional surface model of the bone at the potential dental implant receptor sites based on the at least point-wise digital representation of soft tissue thickness, and generating a single digital project file comprising at least the digitized representation of the intra-oral surface anatomy of the patient, the mapped two-dimensional dental X-ray image and the three-dimensional surface model of the bone at the potential dental implant receptor sites.

An advantage of the present invention is that it does not require costly CT equipment and measurements, while still providing information about the bone structure.

The method according to embodiments of the present invention does not require the use of volumetric imaging techniques such as e.g. CT (computed tomography), cone-beam CT imaging or MRI (magnetic resonance imaging). As CT scans submit the patient to a significant radiation loading, avoiding them is advantageous for the patient. Patient specific information, which may possibly be obtained from different sources such as e.g. optical scanning, digital photography, non-volumetric X-ray etc., may be combined in a digital manner for obtaining a single digital project that can be used by e.g. a clinician in maxillofacial planning software for the purpose of simulating a surgical intervention such as dental implant placement.

The digitized representation of an intra-oral surface anatomy may be investigated for possible dental implant receptor sites.

The digitized representation of an intra-oral surface anatomy may be for the entire dental arch of the upper jaw and/or lower jaw.

According to embodiment of the invention, the digitized representation of an intra-oral surface anatomy may be a surface scan, e.g. an optical scan, e.g. optical surface scan, of the mouth of the patient.

According to other embodiments of the invention, the digitized representation of an intra-oral surface anatomy may be obtained from an impression of the upper jaw and/or lower jaw, whereby this impression may be used to digitally capture spatial coordinates of the intra-oral surface.

The digital representation of the soft tissue may be obtained via statistical information from an expert system.

According to other embodiments, the soft tissue may have a thickness and the digital representation of the soft tissue thickness may be obtained via local measurements of the thickness of the soft tissue. According to embodiments of the invention, the local measurements of the thickness of the soft tissue may be obtained by using a depth gauge, such as, for example at least one hypodermic needle. According to other embodiments of the invention, the local measurements of the thickness of the soft tissue may, for example, be obtained from ultrasound measurements.

According to embodiments of the invention, there being a curved surface following the dental arc, mapping the dental X-ray image along at least part of the dental arch may be performed by folding the dental X-ray image along the curved surface.

Mapping the dental X-ray image along at least part of the dental arch may comprise indicating corresponding points on the dental X-ray image and on the intra-oral surface anatomy.

Mapping the dental X-ray image along at least part of the dental arch may comprise non-uniform stretching of the X-ray image.

According to embodiments of the invention, mapping the dental X-ray image along at least part of the dental arch may include linear scaling of the X-ray image in the apical-coronal-direction or Y-direction of the patient. According to other embodiments of the invention, mapping the dental X-ray image along at least part of the dental arch may include non-linear scaling of the X-ray image in the horizontal direction or X-direction.

Constructing a three-dimensional surface model of the bone at the potential dental implant receptor sites may be performed by offsetting the soft tissue thickness inwardly in a direction towards the jawbone.

Generating a single digital project file comprising information obtained in the previous steps may be performed by combining obtained digital information in a single digital project visualisable on a display screen.

According to embodiments of the invention, the method may furthermore comprise importing the digital project file into implant planning software.

In a second aspect of the invention, a computer program product is provided for executing any of the methods according to the present invention when executed on a computing device associated with a simulation device for simulation of dental implant placement.

The present invention also provides a machine readable data storage device storing the computer program product according to the present invention.

Furthermore, the present invention provides transmission of the computer program product according to the present invention over a local or wide area telecommunications network.

The present invention furthermore provides a computer system for creating a personalized digital planning environment for simulation of dental implant placement from (i) a digitised representation of an intra-oral surface anatomy of a patient including at least a part of the dental arch, (ii) an at least point-wise digital representation of soft tissue thickness in the region of and around potential dental implant receptor sites, and (iii) a two-dimensional dental X-ray image of the potential dental implant receptor sites, the system comprising:

means for mapping the two-dimensional dental X-ray image of the potential dental implant receptor sites along at least part of a dental arch of the digitised intra-oral surface anatomy, means for constructing a three-dimensional surface model of the bone at the potential dental implant receptor sites based on the at least point-wise digital representation of soft tissue thickness, and means for generating a single digital project file comprising at least the digitized representation of the intra-oral surface anatomy of the patient, the mapped two-dimensional dental X-ray image and the three-dimensional surface model of the bone at the potential dental implant receptor sites.

The means for mapping the two-dimensional dental X-ray image may comprise means for investigating for possible dental implant receptor sites.

The means for mapping the two-dimensional dental X-ray image may comprises mean for performing a surface scan of the mouth of a patient.

The means for mapping the two-dimensional dental X-ray image may comprise means for performing linear scaling of the X-ray image in the apical-coronal direction of the patient.

The means for mapping the two-dimensional dental X-ray image may comprise means for performing non-linear scaling of the X-ray image in the horizontal direction.

The soft tissue may have a thickness and the means for constructing a three-dimensional surface model of the bone at the potential dental implant receptor sites may comprise means for local measurement of the thickness of the soft tissue.

The means for constructing a three-dimensional surface model of the bone at the potential dental implant receptor sites may comprise means for performing offsetting the soft tissue thickness inwardly in a direction towards the bone.

The means for generating a single digital project file may comprise means for combining obtained digital information in a single digital project visualisable on a display screen.

The computer system may furthermore comprise means for importing the digital project file into implant planning software.

In still a further aspect of the present invention, a method is provided for creating a personalized digital planning environment for simulation of dental implant placement, the method comprising:

digitising intra-oral surface anatomy of a patient, generating an at least point-wise digital representation of soft tissue thickness in the region of and around potential dental implant receptor sites, taking a two-dimensional dental X-ray image of the potential dental implant receptor sites and mapping it along at least part of a dental arch of the digitised intra-oral surface anatomy, constructing a three-dimensional surface model of the bone at the potential dental implant receptor sites based on the at least point-wise digital representation of soft tissue thickness, and generating a single digital project file comprising information obtained in the previous steps.

The terms "carrier medium" and "computer readable medium" as used herein refer to any medium that participates in providing instructions to a processor for execution. Such a medium may take many forms, including but not limited to, non-volatile media, volatile media, and transmission media. Non-volatile media includes, for example, optical or magnetic disks, such as a storage device which is part of mass storage. Volatile media includes dynamic memory such as RAM. Transmission media include coaxial cables, copper wire and fiber optics, including the wires that comprise a bus within a computer. Transmission media can also take the form of acoustic or light waves, such as those generated during radio wave and infra-red data communications.

Common forms of computer readable media include, for example a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read.

Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infra-red signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the internet. Transmission media can take the form of acoustic or light waves, such as those generated during radio wave and infrared data communications. Transmission media include coaxial cables, copper wire and fibre optics, including the wires that form a bus within a computer.

It is an advantage of embodiments of the present invention that no volumetric scan such as CT or CT-like scanning needs to be performed in order to obtain the required information.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
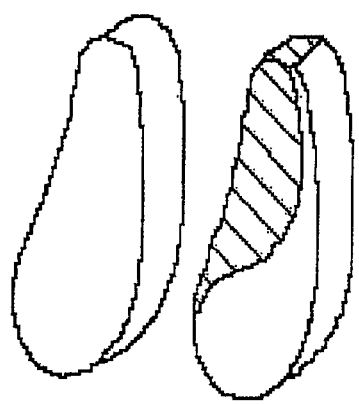
FIG. 1 shows two cross-sections of parts of jawbones which would generate equal X-ray images.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Several embodiments of methods for creating a personalised digital planning file for simulation of a dental implant placement are now described.

Figure 13:
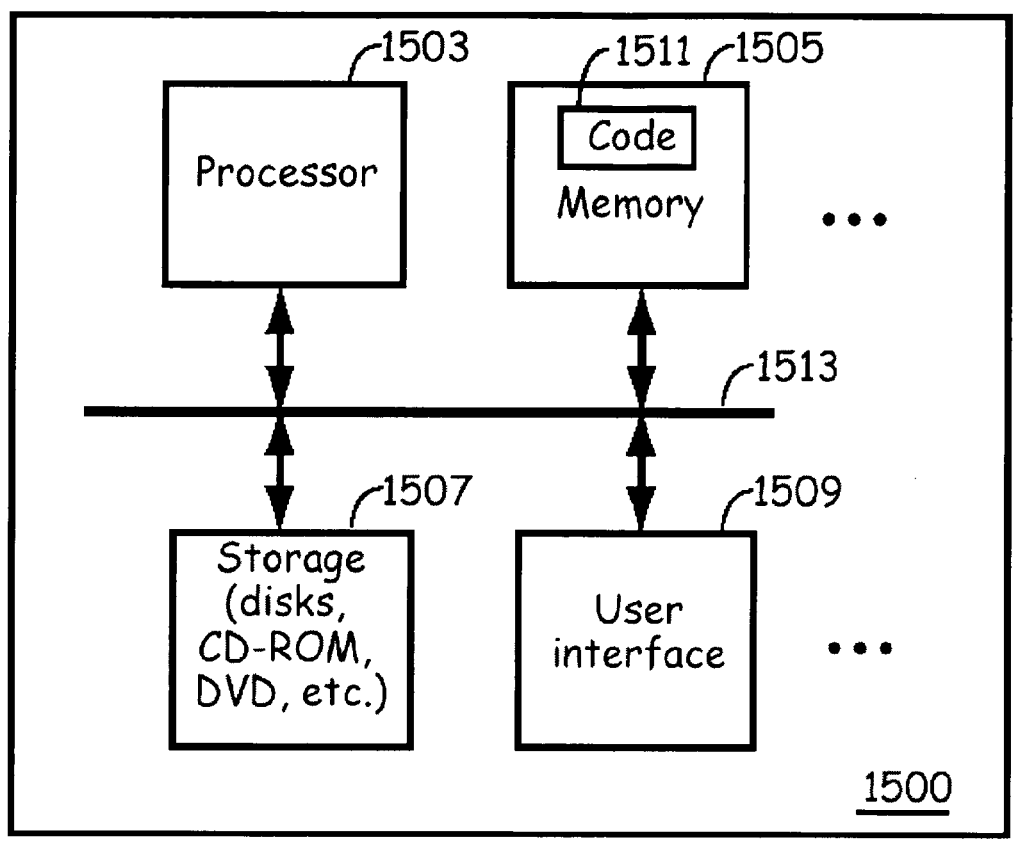
FIG. 13 illustrates a processing system which can be used with methods according to embodiments of the present invention.

Such method embodiments may be implemented in a processing system 1500 such as shown in FIG. 13. FIG. 13 shows one configuration of processing system 1500 that includes at least one programmable processor 1503 coupled to a memory subsystem 1505 that includes at least one form of memory, e.g., RAM, ROM, and so forth. A storage subsystem 1507 may be included that has at least one disk drive and/or CD-ROM drive and/or DVD drive. In some implementations, a display system, a keyboard, and a pointing device may be included as part of a user interface subsystem 1509 to provide for a user to manually input information. Ports for inputting and outputting data also may be included. More elements such as network connections, interfaces to various devices, and so forth, may be included, but are not illustrated in FIG. 13. The various elements of the processing system 1500 may be coupled in various ways, including via a bus subsystem 1513 shown in FIG. 13 for simplicity as a single bus, but will be understood to those in the art to include a system of at least one bus. The memory of the memory subsystem 1505 may at some time hold part or all (in either case shown as 1511) of a set of instructions that when executed on the processing system 1500 implement the step(s) of the method embodiments described herein. Thus, while a processing system 1500 such as shown in FIG. 13 is prior art, a system that includes the instructions to implement novel aspects of the present invention is not prior art, and therefore FIG. 13 is not labelled as prior art.

It is to be noted that the processor 1503 or processors may be a general purpose, or a special purpose processor, and may be for inclusion in a device, e.g., a chip that has other components that perform other functions. Also with developments such devices may be replaced by any other suitable processing engine, e.g. an FPGA. Thus, one or more aspects of the present invention can be implemented in digital electronic circuitry, or in computer hardware, firmware, software, or in combinations of them. Furthermore, aspects of the invention can be implemented in a computer program product tangibly embodied in a carrier medium carrying machine-readable code for execution by a programmable processor. Method steps of aspects of the invention may be performed by a programmable processor executing instructions to perform functions of those aspects of the invention, e.g., by operating on input data and generating output data.

Furthermore, aspects of the invention can be implemented in a computer program product tangibly embodied in a carrier medium carrying machine-readable code for execution by a programmable processor. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Volatile media includes mass storage. Volatile media includes dynamic memory such as RAM. Common forms of computer readable media include, for example a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infrared signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

The present invention provides a method for creating a personalized digital planning environment for simulation of dental implant placement without requiring the use of volumetric imaging techniques such as e.g. CT (computed tomography), cone-beam CT imaging or MRI (magnetic resonance imaging). Therefore, patient specific information, which may possibly be obtained from different sources such as e.g. optical scanning, digital photography, non-volumetric X-ray etc., may be combined in a digital manner for obtaining a single digital project that can be used by e.g. a clinician in maxillofacial planning software for the purpose of simulating a surgical intervention such as dental implant placement.

According to the present invention, the method comprises different steps. Hereinafter, these different steps will be described by means of different embodiments.

A first step of the method according to the present invention comprises digitizing an intra-oral topography or surface anatomy of a patient. In other words, the geometry of remaining teeth and soft tissue is digitized in this first step of the method. According to embodiments of the present invention, this information may be obtained at least for possible implant receptor sites, i.e. for places where no teeth are present anymore. According to other embodiments of the invention, this information may be obtained for an entire dental arch of a lower and/or upper jawbone of the patient, this means locations where teeth are still present together with the locations where no teeth are present anymore and where implants may have to be provided.

Figure 2:
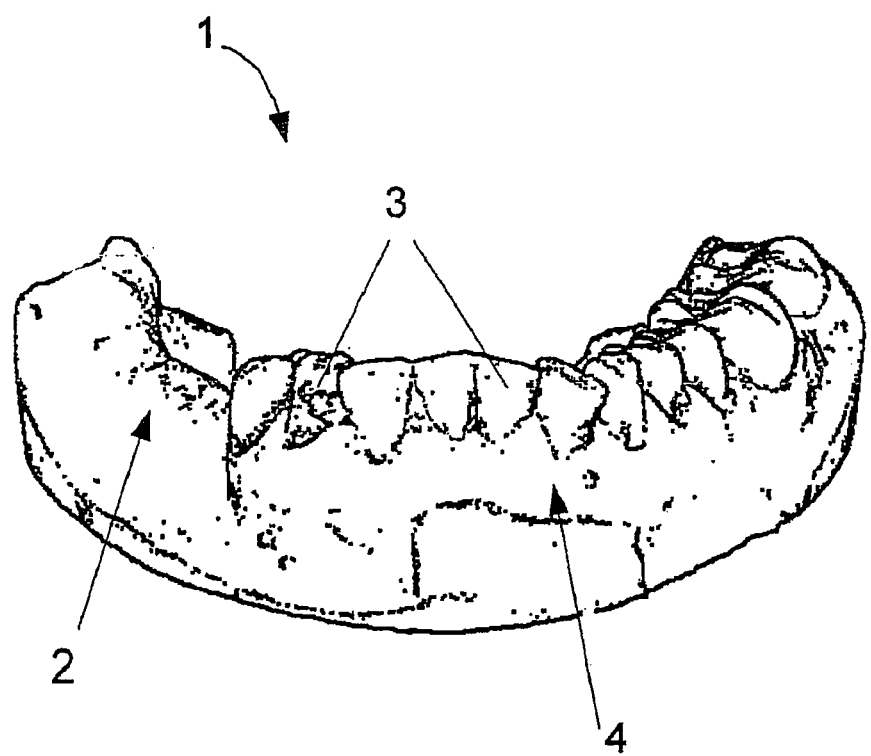
FIG. 2 shows a 3D plaster model of a dental arch.

According to embodiments of the invention, obtaining this information may be done directly, for example by performing an optical scan in the mouth of the patient, e.g. a 3D optical surface scan. According to other embodiments of the invention, obtaining this information may also be done indirectly, for example by taking an impression of the upper and/or lower jaw, converting this impression into a stone or plaster model and digitally capturing spatial coordinates of the intra-oral surface from the stone or plaster model. The latter may be done by means of, for example, a mechanical digitizer, a laser scanner, stereo photography or laser holography. FIG. 2 shows a plaster model of a dental arch 1 comprising potential dental implant receptor sites 2, or locations without teeth 3, and locations 4 where teeth 3 are still present.

The detailed information about the geometry of the remaining dentition and the soft tissue may then be imported into a computer workstation running 3D graphics software. A three-dimensional surface representation of the jaw is thereby obtained. Since the digitization is limited to capturing of the surface geometry, no information is directly available about the position of the jawbone in 3D hidden under the soft tissue after performing this first step of the method according to the invention.

A second step of the method therefore comprises acquiring information about the thickness of the soft tissue, at least in the region of and around potential dental implant receptor sites 2, this, however, without making use of volumetric imaging techniques such as CT, cone-beam CT or MRI.

According to one embodiment of the present invention, information about the thickness of the soft tissue may be obtained via statistical information from an expert system. Therefore, information about the thickness of the soft tissue or gum at different sites along the jaw may be imported from the expert system. The expert system may comprise a database of information about typical soft tissue thickness distributions in different cross-sections along the jaw taken from a representative sample of the population, e.g. recorded depending upon relevant parameters such as age, sex, weight, relevant dimensions of the human subject, e.g. dimensions of patient anatomy, diseases (e.g. gingivitis), etc. For example, statistics may be available for facial soft tissue thickness, based on measurements on cadavers and described in, for example, Domaracki M., Stephan C.: "Facial Soft Tissue Thicknesses in Australian Adult Cadavers", J Forensic Sci, January 2006, Vol. 51, No. 1, pp. 5-10. Such a database may be analysed according to well know statistical techniques to obtain representative values with an optional standard deviation to assist in making decisions. Such captured soft tissue thicknesses or thickness distributions can be correlated with the soft tissue thickness visible in projection in the axial direction of an X-ray image, i.e. from the crest of the jawbone to the delineated gingival level. In providing values for use with the present invention the expert system may take information into account, and/or provide information about, variations in soft tissue distributions related to suitable parameters, e.g. age, gender, diseases (e.g. gingivitis), patient anatomy, etc.

Figure 3:
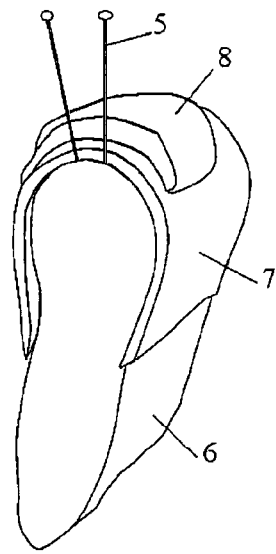
FIG. 3 illustrates part of a jawbone covered with soft tissue and an impression material, needles for measuring the soft tissue thickness being provided through the impression material and the soft tissue.

According to another embodiment the thickness of the soft tissue may be measured using a depth gauge such as, for example, at least one hypodermic needle 5 or the like, in discrete points. This is illustrated in FIG. 3, which shows a part of a jawbone 6 with soft tissue 7 on top of it. Preferably, the depth gauge, e.g. hypodermic needle(s) 5, may be provided through a silicone or alginate impression material 8 which is seated in the mouth of the patient. A set of hypodermic needles 5 may then be used which remain fixed in the impression material 8 after removal form a patient's mouth. The hypodermic needles 5 indicate the direction of the measurement while the level (depth) of intrusion in the soft tissue 7 can be determined relative to the remaining dentition or other reference points in the jaw such as, for example, old or temporary implants.

Figure 4:
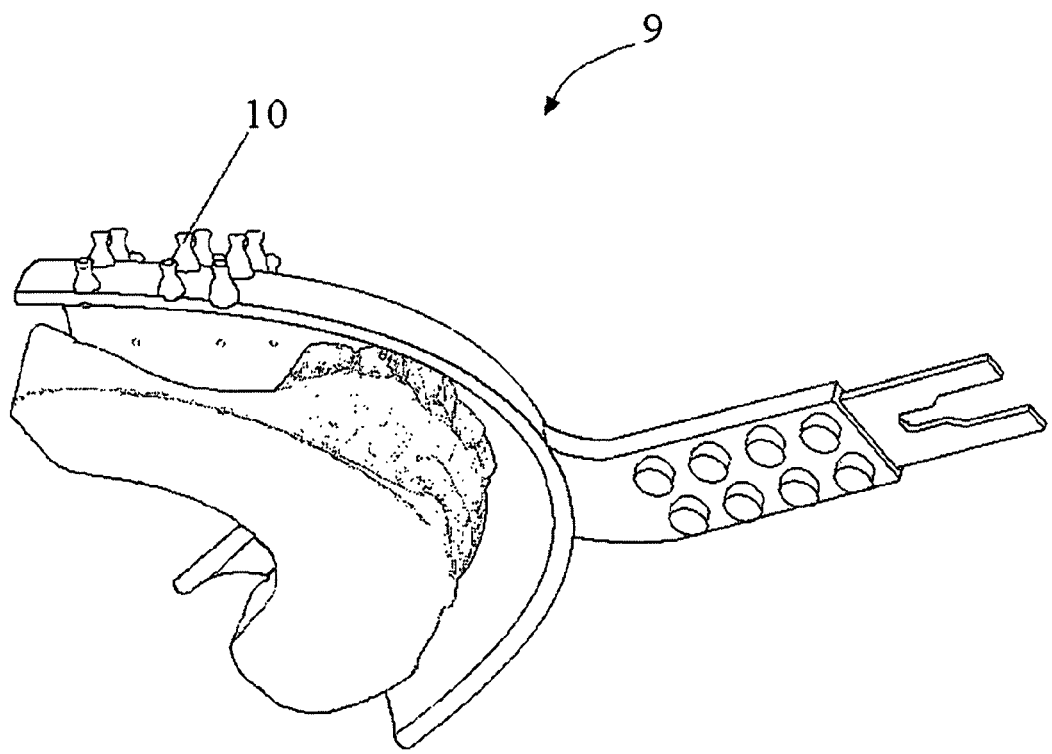
FIG. 4 illustrates an impression tray which can be used for measuring the soft tissue thickness in accordance with embodiments of the invention.

Alternatively, an impression tray 9 with gauging cylinders 10 for guiding the hypodermic needle(s) 5 along a predetermined path may be used. This is illustrated in FIG. 4. The impression tray 9 may be filled with an impression material, such as e.g. silicone or alginate paste (not shown in FIG. 4), and the patient bites down on it to create an impression in the impression material. This is identical to known, conventional ways of working. Measurements may be performed through the impression tray 9 and the impression material and may be recorded.

According to yet another embodiment, ultrasound measurements may be used to locally quantify the thickness of the soft tissue 7. Ultrasound thickness measurements are well known to a person skilled in the art.

The present invention also includes using a combination of two or more of the methods mentioned above. For example, one method may be used as a main method and a second method used for corroboration of the results. This may be advantageous when the main method does not provide enough or accurate points. These can then be improved by regression against known values from an expert system, for example.

Figure 5:
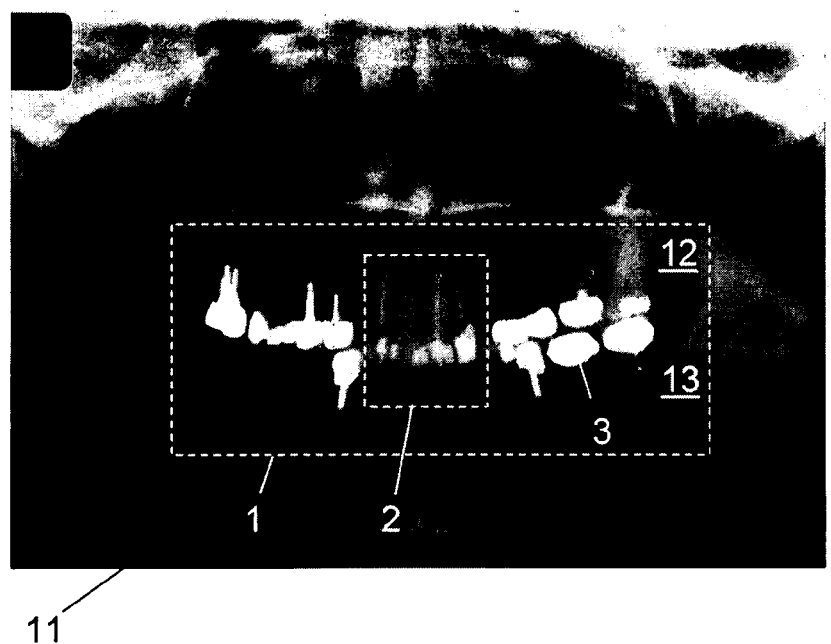
FIG. 5 shows an X-ray image of a mouth of a patient.

During a third step of the method according to the invention, a two-dimensional (2D) dental X-ray image of at least the potential dental receptor sites 2, but preferably of the entire dental arch 1, is acquired, and the thereby obtained image is mapped along at least part of the dental arch 1 as determined on the 3D digital representation of the intro-oral topography, e.g. the 3D digital representation of the plaster model. According to preferred embodiments of the invention, the 2D dental X-ray image may be mapped along the entire dental arch 1, thereby providing a 2D dental X-ray image map of all locations 4 with teeth 3 or old or temporary implants and all locations providing potential dental receptor sites 2. FIG. 5 illustrates a dental X-ray image 11 of a complete mouth of a patient, i.e. of the upper jaw 12 and lower jaw 13 showing potential dental implant receptor cites 2 and locations where teeth 3, or possibly old or temporary implants, are present.

Figure 6:
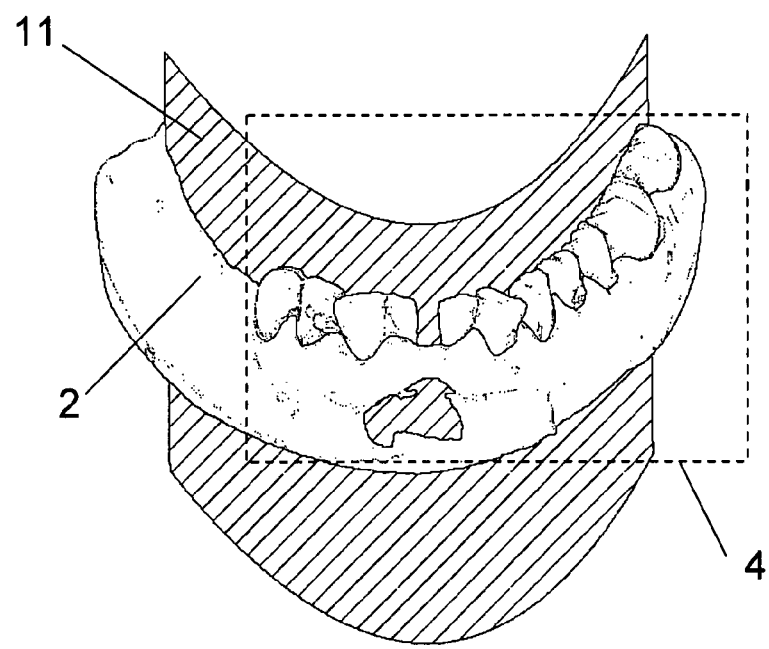
FIG. 6 (front view) and FIG. 7 (top view) illustrate how an X-ray film is folded on a curved surface that follows the arch of the jaw of a patient, for obtaining a panoramic X-ray image.
Figure 7:
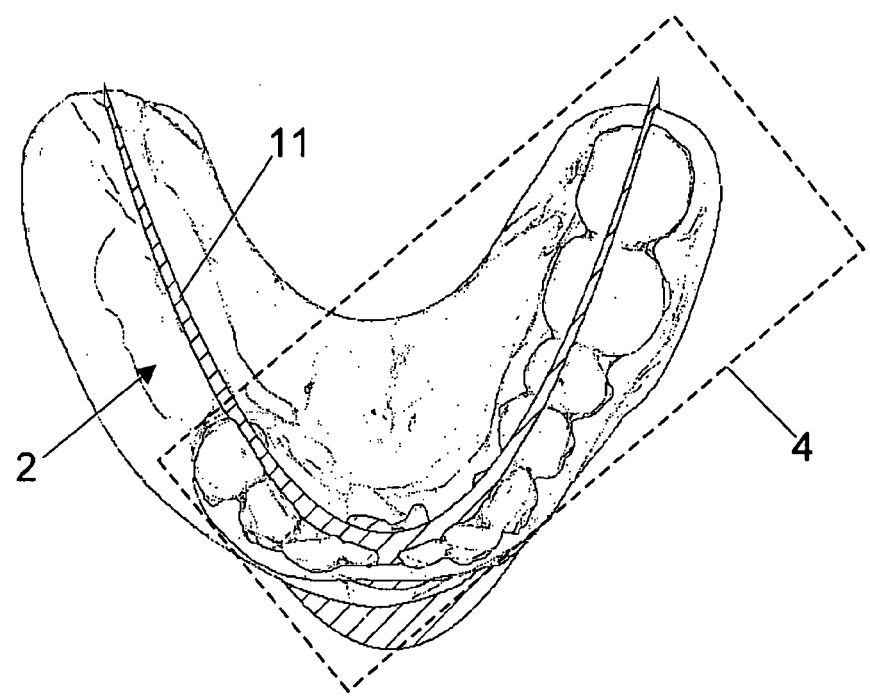
Figure 8:
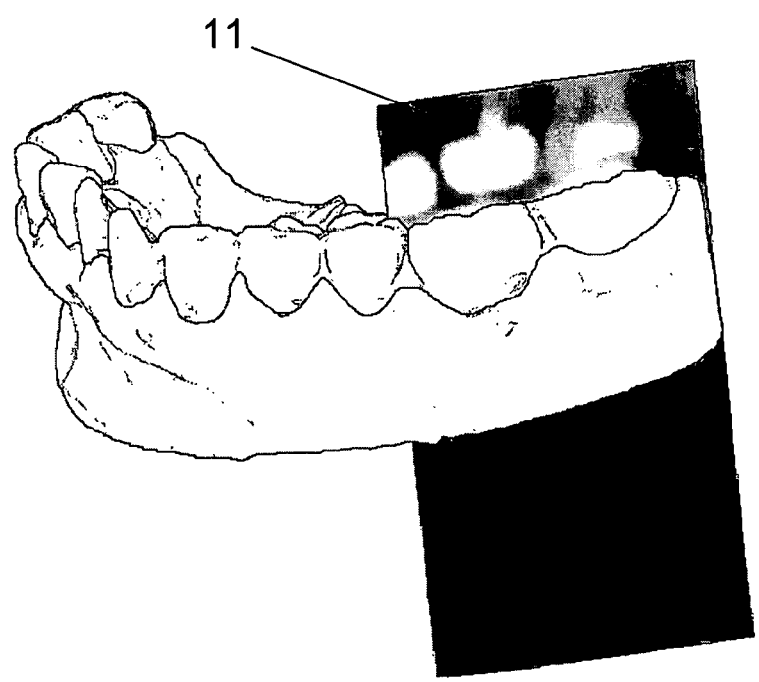
FIG. 8 illustrates the mapping of a panoramic X-ray image on a 3D representation of the intra-oral surface anatomy.

According to one embodiment of the invention, mapping of the X-ray image to the patient anatomy may be performed including non-uniform (may be linear or non-linear) scaling and deformation of the X-ray image 11. Therefore, the X-ray film 11 may be interpreted as being folded along a curved internal surface of the dental arch 1, the curved surface following the arch 1 of the jaw. This is illustrated in FIGS. 6 (front view) and 7 (top view). The 2D dental X-ray image 11 may be a panoramic X-ray image. As the panoramic X-ray image may be subject to magnification errors and errors due to the variation of the patient from the scanning equipment or even displacement of the patient while taking the X-ray image, distortions may be present in the 2D dental X-ray image 11. Especially in the horizontal direction, there may be non-linear variations in the magnification at different object depths. To obtain an accurate mapping of the panoramic X-ray image 11 with respect to the 3D representation of the treatment area, i.e. the region of and around potential dental implant receptor sites 2, the mapping method must allow non-uniform stretching of the X-ray image 11. A possible approach may be to indicate pairs of corresponding points with a first point of the pair on the X-ray image 11 and a second point of the same pair on the 3D representation obtained during the first step of the method. Where these points are indicated, the correspondence between the X-ray image 11 and the 3D representation will be accurate. In regions between the points and/or away from the points, the X-ray image 11 may be interpolated, respectively extrapolated, to obtain minimal distortion of the X-ray image 11. A mathematical optimization approach of interpolation with RBF e.g. (Radial Base Function) functions can be used to obtain this mapping. This embodiment is illustrated in FIG. 8.

According to embodiments the mapping may be performed in a linear manner according to the axial direction or Z-direction, i.e. the apical-coronal direction relative to the teeth, and in a non-linear manner in the horizontal or X-direction. Preferably, mapping may be performed in a linear manner in the Z-direction because typically X-ray images are relatively accurate in the Z-direction (see 'Implants and Restorative Dentistry', Chapter 11—Imaging in oral implantology, page 178 mentioned above), in which it is described that performing measurements in the X-direction is not reliable, but performing measurements in the Z-direction is reliable. Performing measurements in the Y-dimension does not give data. The mapping may be based on a calibration element with known length and visible in the X-ray image along the Z-direction. Such fiducial markers are known to the skilled person.

In a fourth step of the method according to the invention, a 3D surface model of the jawbone at potential dental implant receptor sites 2 is created based on the soft tissue thickness information acquired during the second step of the method according to the invention, at the region of and around potential dental implant receptor sites 2.

Figure 9:
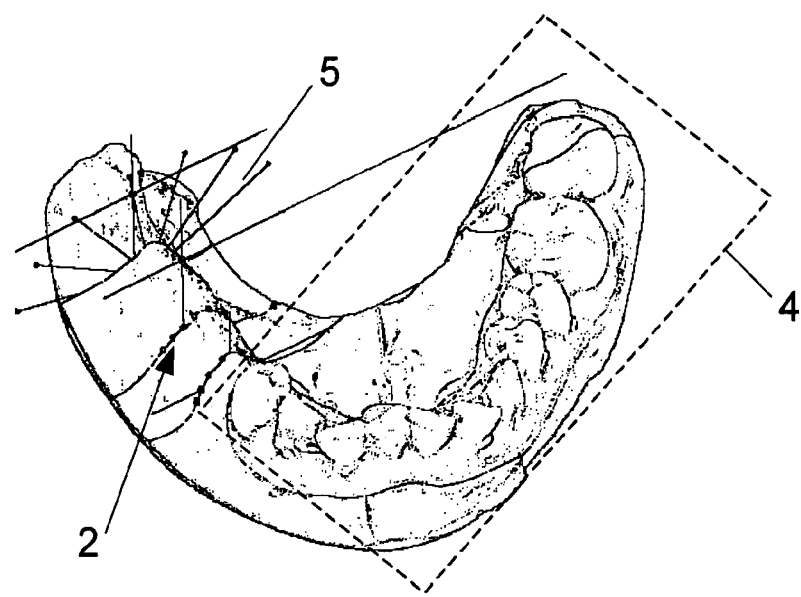
FIG. 9 illustrates a set-up with needles for determining soft tissue thickness.
Figure 10:
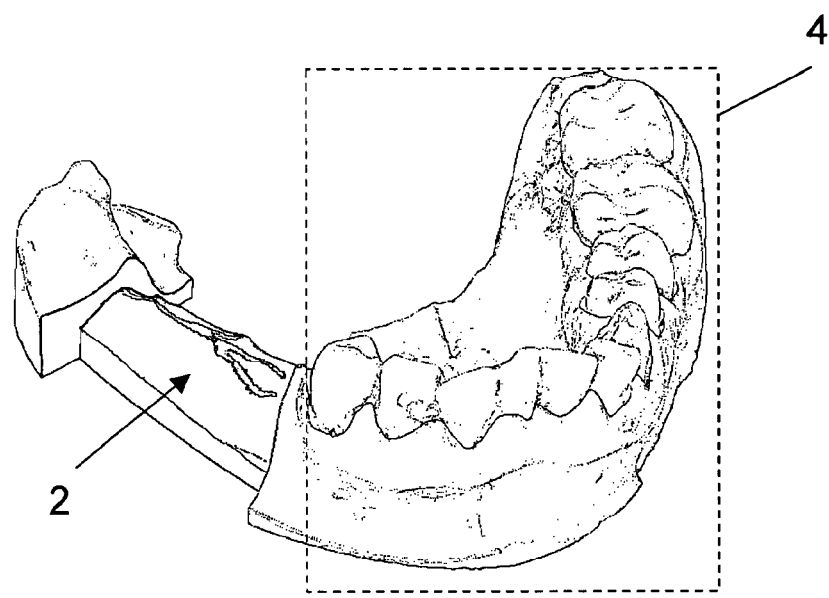
FIG. 10 illustrates determined bone structure of the jaw, obtained by offsetting the known soft tissue surface inward over a distance known from the measurements of soft tissue thickness.

According to one embodiment of the invention, this creating of a 3D surface model of the jawbone may be made by offsetting from the soft tissue surface, known from the digitized plaster model or the optical scan, in an inward direction, i.e. from the soft tissue surface towards the underlying bone. This offset is over distances known from statistical values provided in the second step or from the measurements performed in the second step (see FIG. 9). In the case of using the results of the measurements performed in the second step of the method, the exact offset value may be known for tissue points lying on the measurement axes, i.e. the axes determined by the hypodermic needles and their placement in the soft tissue during measurement. For the other points, i.e. points not lying on the measurement axes, but rather in between hypodermic needles, the offset value may be interpolated between known offset values in the discrete measuring points. Any suitable interpolation method can be used, e.g. polynomial interpolation. The result is a 3D surface model of the jawbone at the region of and around potential dental implant receptor sites 2 as illustrated in FIG. 10.

According to another embodiment of the invention, the thickness of the soft tissue 7 may be measured on the available X-ray image 11 in different points along the dental arch 1. These measurements may be transferred to the 3D digital representation of the intra-oral topology and may be assumed constant in a section perpendicular to the dental arch 1, i.e. in the cross-sections or the observed values may be input into the expert system mentioned above and used to obtain adjusted values of the soft tissue thickness by extrapolating known values to values at other positions not visible on the X-ray image.

According to another embodiment of the invention, the digital representation of the bone may be generated starting from the cross-section of the digital representation of the 3D stone or plaster model or of the optical scan, i.e. the intra-oral topography with soft tissue being present. By respectively offsetting the contours inwards with a constant or adjusted thickness as measured applicable in that section during the second step of the method, a set of contours is obtained defining the shape of the bone of the jaw. Using a lofting operation these contours can be used to generate a 3D representation of the bone of the jaw. With lofting operation is meant connecting two polygonal contours together with a triangular mesh, in that way producing a surface.

According to yet another embodiment of the present invention, a hollowing operation may be applied to the 3D representation of the stone or plaster model or to the optical scan that forms the 3D model of the intra-oral topography with soft tissue in place. Such a hollowing operation creates an inner surface that is uniformly offset relative to the stone or plaster model. This inner surface may be regarded as a simplified representation of the bone assuming a constant thickness of the soft tissue 7 over the entire jaw.

Figure 11:
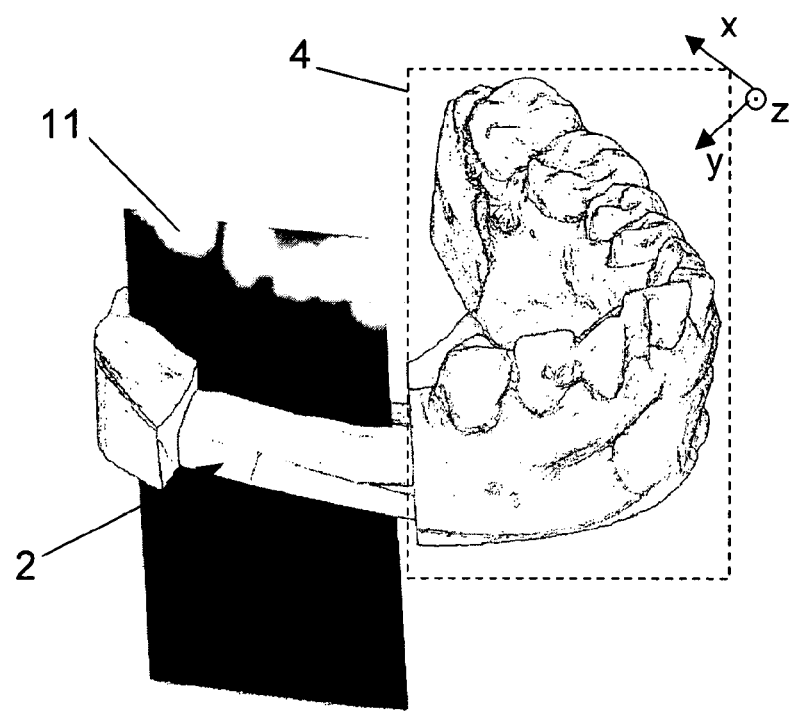
FIG. 11 illustrates mapping an X-ray image with the determined bone structure.

A fifth step of the method according to the present invention is generating a single digital project file that comprises a combination of at least the digital representation of the plaster model or the optical scan, i.e. of the intra-oral topography, the mapped X-ray image and the digital representation of the bone at the potential dental implant receptor sites 2 as obtained in the previous steps (see FIG. 11). This project file can be imported and used in implant planning software, for example SimPlant™, provided by Materialise, Belgium, for the purpose of simulating implant placement. In other words, the fifth step of the method according to the present invention comprises combining digital information obtained in former steps in a single digital project file to be visualised on a display, e.g. computer screen or printed on a printing device such as a plotter.

Figure 12:
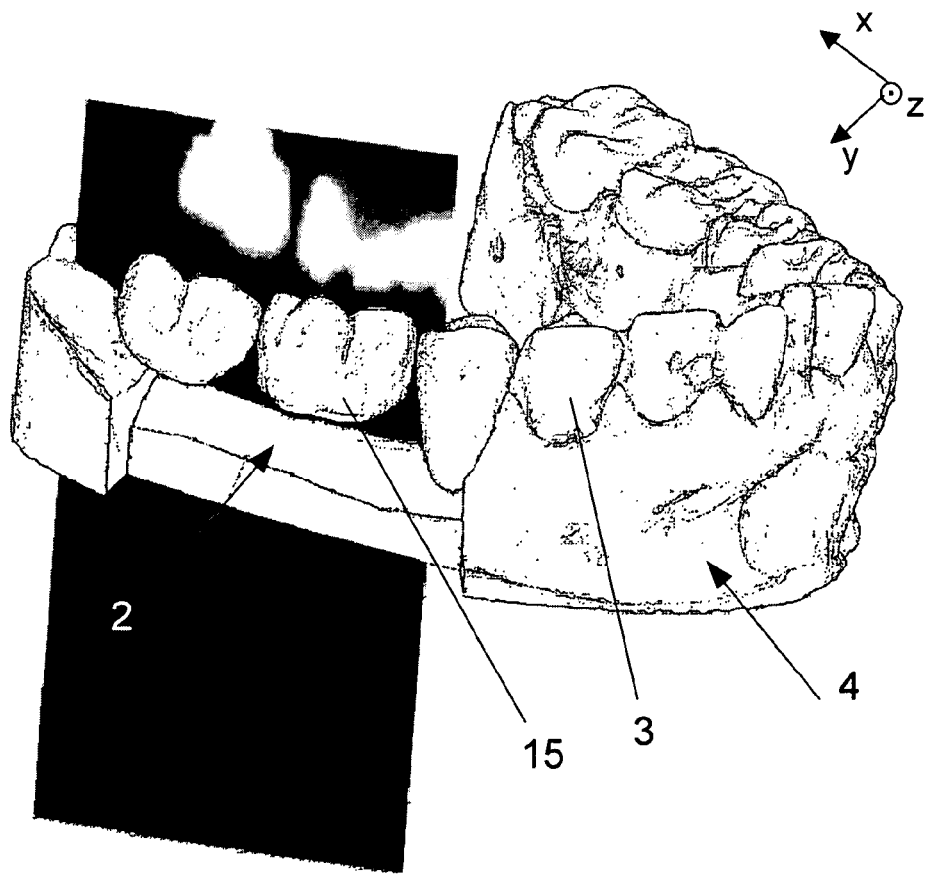
FIG. 12 illustrates addition of a digital representation of an ideal tooth set-up in a receptor site, to aid in the decision where and how to place the implants.

In this planning environment a digital representation of the ideal tooth set-up in the receptor sites 2 may be added, for example from a digital tooth library, to aid in the decision of where and how to place the implants 15, as illustrated in FIG. 12.

After planning, the digital representation of the intra-oral topography, e.g. plaster model or optical scan, may be used to design and produce dedicated surgical templates to assist the surgeon in transferring the implant plan to the patient during a surgical intervention.

An advantage of the present invention is that it does not require costly CT equipment and measurements, while still providing information about the bone structure. CT equipment is not always readily available so that there are dentists who do not have access to CT equipment. As CT scans submit the patient to a significant radiation loading, avoiding them is advantageous for the patient. The present invention therefore provides a safe and more easily available method for creating a personalized digital planning file for simulation of dental implant placement. Moreover, the method according to the present invention allows mapping of an X-ray image to the 3D model of the intra-oral topography in the axial direction or Z-direction, i.e. the apical-coronal direction relative to the teeth, and allows mapping by non-linear scaling and deformation of the X-ray image in the X-direction.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A method for creating a personalized digital planning environment for simulation of dental implant placement, the method comprising:
providing (i) a digitized representation of an intra-oral surface anatomy of a patient including at least a part of the dental arch, (ii) an at least point-wise digital representation of soft tissue thickness in the region of and around potential dental implant receptor sites, and (iii) a two-dimensional dental X-ray image of the potential dental implant receptor sites,
mapping the two-dimensional dental X-ray image of the potential dental implant receptor sites along at least part of a dental arch of the digitized intra-oral surface anatomy, wherein the mapping step comprises indicating corresponding points on the dental X-ray image and on the intra-oral surface anatomy, non-uniform stretching of the X-ray image, and at least one of linear scaling of the X-ray image in the apical-coronal direction of the patient and non-linear scaling of the X-ray image in the horizontal direction,
constructing a three-dimensional surface model of the bone at the potential dental implant receptor sites based on the at least point-wise digital representation of soft tissue thickness, and
generating a single digital project file comprising at least the digitized representation of the intra-oral surface anatomy of the patient, the mapped two-dimensional dental X-ray image, and the three-dimensional surface model of the bone at the potential dental implant receptor sites.

2. The method according to claim 1, wherein:
the digitized representation of an intra-oral surface anatomy is investigated for possible dental implant receptor sites, and/or
the digitized representation of an intra-oral surface anatomy is for the entire dental arch of the upper jaw and/or lower jaw, and/or
the digitized representation of an intra-oral surface anatomy is a surface scan of the mouth of the patient, and/or
the digitized representation of an intra-oral surface anatomy is obtained from an impression of the upper jaw and/or lower jaw, whereby said impression is used to digitally capture spatial coordinates of the intra-oral surface, and/or
the digital representation of the soft tissue is obtained via statistical information from an expert system.

3. The method according to claim 1, wherein the soft tissue has a thickness, and the digital representation of the soft tissue is obtained via local measurements of the thickness of the soft tissue, wherein local measurements of the thickness of the soft tissue are obtained from ultrasound measurements or are obtained by using a depth gauge.

4. The method according to claim 3, wherein the depth gauge comprises at least one hypodermic needle.

5. The method according to claim 1, wherein constructing a three-dimensional surface model of the bone at the potential dental implant receptor sites is performed by offsetting the soft tissue thickness inwardly in a direction towards the jawbone.

6. The method according to claim 1, wherein generating a single digital project file comprising information obtained in the previous steps is performed by combining obtained digital information in a single digital project that can be visualized on a display screen.

7. The method according to claim 1, further comprising importing the digital project file into implant planning software.

8. The method according to claim 1, wherein the dental X-ray image is a panoramic X-ray image.

9. A computer program product for executing the method as claimed in claim 1 when executed on a computing device associated with a simulation device for simulation of dental implant placement.

10. A method for creating a personalized digital planning environment for simulation of dental implant placement, the method comprising:
digitizing intra-oral surface anatomy of a patient,
generating an at least point-wise digital representation of soft tissue thickness in the region of and around potential dental implant receptor sites,
taking a two-dimensional dental X-ray image of the potential dental implant receptor sites and mapping it along at least part of a dental arch of the digitized intra-oral surface anatomy, wherein the mapping step comprises indicating corresponding points on the dental X-ray image and on the intra-oral surface anatomy, non-uniform stretching of the X-ray image, and at least one of linear scaling of the X-ray image in the apical-coronal direction of the patient and non-linear scaling of the X-ray image in the horizontal direction, constructing a three-dimensional surface model of the bone at the potential dental implant receptor sites based on the at least point-wise digital representation of soft tissue thickness, and generating a single digital project file comprising information obtained in the previous steps.

11. The method according to claim 10, wherein the dental X-ray image is a panoramic X-ray image.

* * * * *